United States Patent [19]

Hermecz et al.

[11] 4,452,982
[45] Jun. 5, 1984

[54] PROCESS FOR THE PREPARATION OF NITROGEN-BRIDGEHEAD CONDENSED PYRIMIDINE COMPOUNDS, AND PHARMACEUTICAL COMPOSITIONS CONTAINING THEM

[75] Inventors: Istvan Hermecz; Tibor Breining; Lelle Vasvári née Debreczy; Ágnes Horvath, all of Budapest; József Kökösi, Budaörs, all of Hungary

[73] Assignee: Chinoin Gyogyszer es Vegyeszeti Termekek Gyara R.T., Budapest, Hungary

[21] Appl. No.: 148,238

[22] Filed: May 9, 1980

[30] Foreign Application Priority Data

May 11, 1979 [HU] Hungary .............................. CI 1933

[51] Int. Cl.³ ................. C07D 239/70; A61K 31/505
[52] U.S. Cl. .................................... 544/282; 424/251
[58] Field of Search .................. 544/282; 424/251; 542/454, 455

[56] References Cited

U.S. PATENT DOCUMENTS

| | | | |
|---|---|---|---|
| 3,141,043 | 7/1964 | McBee | 564/250 |
| 3,585,198 | 6/1971 | Meszaros et al. | 424/251 |
| 4,234,586 | 11/1980 | Hermecz et al. | 544/282 |
| 4,260,612 | 4/1981 | Hermecz et al. | 544/282 |

OTHER PUBLICATIONS

British J. Pharm. 46, 56–66 (1972).
Arzneimittelforschung 22, 815–829, (1972).

*Primary Examiner*—Donald G. Daus
*Assistant Examiner*—S. A. Gibson
*Attorney, Agent, or Firm*—Karl F. Ross; Herbert Dubno

[57] ABSTRACT

A process is disclosed for the preparation of compounds of the formula (I)

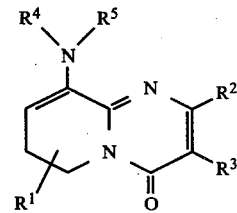

wherein
$R^1$ and $R^2$ are each hydrogen or lower alkyl;
$R^3$ is carboxy, lower alkoxycarbonyl, carbamoyl, carbamoyl substituted by one or two lower alkyl groups, or cyano;
$R^4$ is hydrogen, lower alkyl, phenyl, naphthyl, phenyl or naphthyl substituted by at least one fluoro, chloro, bromo, iodo, lower alkyl, lower alkoxy, hydroxy, carboxy, or phenyl, pyridyl or tetrazolyl; and
$R^5$ is hydrogen or lower alkyl; or a pharmaceutically acceptable salt, hydrate, stereoisomer, optically active isomer, geometric isomer, or tautomer thereof, which comprises the step of aminating a racemic or optically active compound of the formula (II)

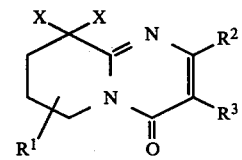

wherein X is halogen with a compound of the formula (III)

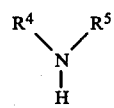

or a pharmaceutically acceptable acid addition salt thereof. The compound of formula (II) possess antiallergic, especially antiasthma, activity.

8 Claims, No Drawings

PROCESS FOR THE PREPARATION OF NITROGEN-BRIDGEHEAD CONDENSED PYRIMIDINE COMPOUNDS, AND PHARMACEUTICAL COMPOSITIONS CONTAINING THEM

The present invention relates to a process for the preparation of nitrogen-bridgehead condensed pyrimidine compounds, the salts hydrates and isomers thereof. The invention also relates to certain representatives of the compounds prepared and pharmaceutical compositions containing them. The compounds possess physiological properties, particularly antiallergic and/or antiasthmatic activity.

According to one feature of the present invention there is provided a new process for the preparation of compounds of the formula

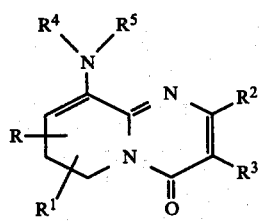  I wherein
  R is hydrogen or lower alkyl,
  $R^1$ is hydrogen, lower alkyl, styryl or carboxy or a derivative thereof;
  $R^2$ is hydrogen or substituted or unsubstituted lower alkyl;
  $R^3$ is hydrogen, substituted or unsubstituted lower alkyl, aryl, aralkyl, halogen, carboxy or a derivative thereof, or the group —$(CH_2)_m$—COOH (in which m is the integer 1, 2 or 3) or a carboxy derivative thereof, formyl, lower alkanoyl or a condensed derivative thereof;
  $R^4$ is hydrogen, substituted or unsubstituted alkyl, aryl which can be substituted by one or more substituents, substituted or unsubstituted aralkyl, a heterocyclic group which can be substituted by one or more substituents or the group —$(CH_2)_m$—Het (in which m is the interger 1, 2 or 3, Het is a substituted or unsubstituted heterocyclic group;
  $R^5$ is hydrogen, lower alkyl, aryl which can be substituted by one or more substituents, formyl, lower alkanoyl, substituted or unsubstituted aroyl or heteroaroyl; or
  $R^4$ and $R^5$ together wlith the nitrogen therebetween form a substituted or unsubstituted mono- or bicyclic heterocyclic ring which can contain also a further heteroatom.

It will be appreciated that the compounds of the formula I may exist in the form of their stereoisomers, optically active isomers, geometric isomers, tautomers and racemic mixtures. The preparation of all such forms of the compounds of formula I and the salts and hydrates thereof is within the scope of the present invention.

According to the invention the compounds of the formula I, pharmaceutically acceptable salts thereof, hydrates, optically active, geometric and stereoisomers and tautomers thereof are prepared by reacting a racemic or optically active compound of the formula

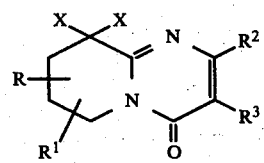  (II)

wherein X is halogen—with a compound of the formula

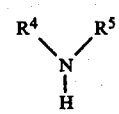  (III)

or an acid addition salt thereof, and if desired, converting a compound of the formula I into a pharmaceutically acceptable salt thereof; liberating a compound of the formula I from a salt thereof; and/or separating a racemate of the formula I into its optically active antipodes.

The term "lower alkyl" used herein for alkyl groups or alkyl-containing groups generally stands for $C_{1-6}$, preferably $C_{1-4}$ straight or branched chain aliphatic saturated hydrocarbons, such as methyl, ethyl, n-propyl, isoproyl, n-butyl, secondary butyl, tertiary butyl, n-pentyl, neo-pentyl, and n-hexyl.

The term "derivative of a carboxy group" stands for conventional carboxylic acid derivatives such as alkoxycarbonyl, e.g. lower alkoxycarbonyl, aryloxycarbonyl, aralkoxycarbonyl or other esters, carbamoyl optionally substituted by one or two alkyl (e.g. lower alkyl), aryl or aralkyl groups; cyano, carboxylic acid hydrazido or hydroxamic acid (—CO—NHOH).

The term "aryl" used as such or in aryl-containing groups such as aryloxy can be substituted or unsubstituted $C_{6-10}$ aromatic groups, such as phenyl or naphthyl or substituted derivatives thereof.

The term "aralkyl" used as such or in aralkyl-containing groups, such as aralkyloxy, can be $C_{1-3}$ alkyl substituted by phenyl or naphthyl, such as benzyl, β-phenylethyl, α,β-diphenyl-ethyl, β,β-diphenyl-ethyl, etc.

The term "lower alkanoyl condensed derivative" as used herein means a lower alkanoyl condensed with a primary or secondary amine, for example dimethylamine, N-methylaniline.

The term "substituted alkyl" as used herein means alkyl substituted by hydroxy, halogen, carboxy or derivatives thereof, amino, substituted amino, alkoxy, or alkanoyloxy, such as trifluoromethyl, hydroxyethyl, aminoethyl, carboxymethyl, and β-carboxyethyl.

The term "lower alkanoyl" as used herein means groups containing 1 to 4 carbon atoms in the alkyl moiety, preferably alkane carboxylic acid radicals, such as formyl, acetyl, propionyl, and butyryl.

The term "aroyl" represents acid radicals of aromatic carboxylic acids, such as substituted or unsubstituted benzoyl groups.

The term "heteroaryl" can stand for heterocyclic carboxylic acid radicals, such as pyridine-2-, 3- or 4-carboxylic acid, furan-carboxylic acid, etc.

The term "heterocyclic group" stands for mono- or bicyclic rings containing 1 to 4 nitrogen, oxygen and/or sulfur atoms, being substituted or unsubstituted aromatic or partially or completely saturated rings, such as thienyl, furyl, pyrrolyl, pyridyl, pyrimidinyl, pyrazinyl, quinolyl, isoquinolyl, benzofuranyl, benzoxazolyl, oxazolyl, oxydiazolyl, imidazolyl, benzimidazolyl, indolyl, benzothiazolyl, benzisothiazolyl, tetrazolyl, thiadiazolyl, triazinyl, piperidinyl, moropholinyl, pirrolydinyl, piperazinyl and N-methylpiperazinyl.

The term "heteroaryl" means mono- or bicyclic substituted or unsubstituted aromatic ring-system containing 1 to 4 nitrogens, oxygens and/or sulfur atoms, such as thienyl, furyl, pyrrolyl, pyridyl, pyrimidinyl, pyrazinyl, pyridazinyl, quinolyl, isoquinolyl, benzofuranyl, benzoxazolyl, oxazolyl, oxadiazolyl, imidazolyl, benzimidazolyl, indolyl, benzotriazolyl, benzisothiazolyl, tetrazolyl, thiadiazolyl and triazolyl.

The group —$NR^4R^5$ stands for a five- or six-member optionally condensed group, optionally containing further nitrogen, oxygen or sulphur, for example pyrrolyl, pyrrolydinyl, pyrrolinyl, piperidinyl, morpholinyl, thiomorpholinyl, 1,2,3,4-tetrahydro-quinolyl, and 1,2,3,4-tetrahydro-isoquinolyl.

The aryl groups, the aryl group of the aralkyl groups and the hetercyclic groups may be substituted by one of more suitable groups or atoms, such as halogen, e.g. chlorine, bromine, iodine or fluorine; lower alkyl, e.g. methyl, ethyl; lower alkoxy, e.g. methoxy, ethoxy; lower alkylenedioxy, e.g. methylenedioxy, ethylenedioxy or propylenedioxy; mono-, di- or trihalogenalkyl, e.g. trifluoromethyl; amino, alkanoylamino, substituted amino, carboxy or derivatives thereof, sulfonic acid or salt, ester thereof, hydroxy, alkanoyloxy aroyloxy, heteroaroyloxy, nitro, mercapto, and lower alkylthio, etc.

Preferred compounds which can be prepared by the process according to the invention by virtue of their especially favorable physiological activity include compounds of the formula I wherein R is hydrogen,
$R^1$ is hydrogen, lower alkyl, preferably methyl, styryl or lower alkoxycarbonyl, preferably methoxycarbonyl or ethoxycarbonyl;
$R^2$ is hydrogen, lower alkyl, preferably methyl;
$R^3$ is carboxyl, lower alkoxycarbonyl, preferably methoxycarbonyl, or ethoxycarbonyl, carbamoyl, cyano, formyl, lower alkyl, preferably methyl, or phenyl;
$R^4$ is hydrogen, lower alkyl, preferably methyl, hydroxyethyl, carboxyalkyl, optionally substituted phenyl or naphthyl, trifluoromethyl, benzyl, 2-, 3- or 4-pyridyl, benzothiazol-2-yl, methoxycarbonyl or ethoxycarbonyl;
$R^5$ is hydrogen, lower alkanoyl, preferably acetyl, benzoyl or nicotinoyl, or
the group —$NR^4R^5$ stands for piperidinyl, pyrrodinyl, morpholinyl,
$R^4$ preferably represents phenyl, which may be substituted in the o-, m- and/or p-position
by one, two or three of the following substituents: hydroxyl, carboxy or a derivative thereof, alkoxy, alkylenedioxy, amino, substituted amino, nitro, trifluoromethyl, halogen, lower alkyl, sulfonic acid group.

In an especially preferred class of compounds of the formula I, R represents hydrogen, $R^1$ represents 6-methyl, $R^2$ is hydrogen, $R^3$ is carboxy, $R^4$ is an optionally substituted phenyl, $R^5$ is hydrogen. Pharmaceutically acceptable salts of these compounds are also preferred.

Compounds of the formula I containing carboxy or sulfonic acid groups form salts which pharmaceutically acceptable bases, such as alkali metal salts, e.g. sodium or potassium salts, alkali earth metal salts, e.g. calcium or magnesium salts, ammonium salts; and with organic amines, such as triethylamine salts, ethanol amine salts, etc.

The invention provides a method for the preparation of the optical and geometric isomers and tautomers or the compound of the formula I as well. The structure of the geometric isomers is represented by formula

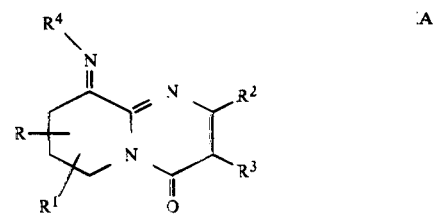

and by formula

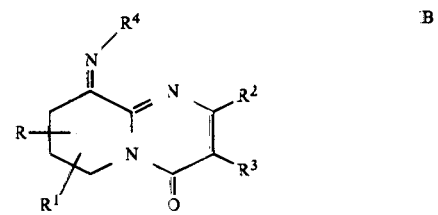

($R^5$ = hydrogen)

The structure of the tautomers is shown by the relationship A:

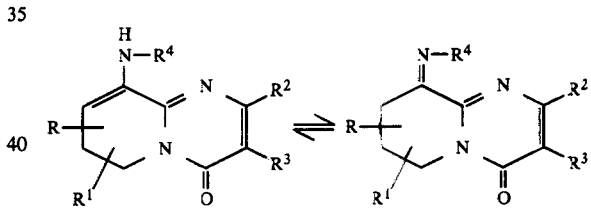

($R^5$ = hydrogen)

In the compounds of the formula II used as starting materials for the preparation of the compounds of the formula I, X preferably is chlorine, bromine or iodine.

The compound of the formula III is preferably used in an amount of 1 of 3 molar equivalent. The reaction of compounds of the formulae II and III is preferably conducted in the presence of an acid binding agent. As acid binding agents preferably alkali metal carbonates, such as sodium or potassium carbonate, alkali metal hydrogen carbonates, such as sodium or potassium hydrogen carbonate, alkali metal salts of weak acids, such as sodium acetate, organic bases, such as N-methylaniline, triethyl amine, pyridine are used. An excess of the starting compound of the formula III can also be used as an acid binding agent.

The reaction can optionally be conducted in an inert organic solvent. As a reaction medium preferably aromatic hydrocarbons, such as benzene, toluene, xylene, esters, such as ethyl acetate, alohols, such as methanol, ethanol, dimethyl foramide, dimethyl sulfoxide, or halogen containing hydrocarbons, such as chloroform, dichloromethane, dichloroethane, chlorobenzene may be used.

The reaction is performed at 0° to 200° C., preferably at room temperature, or at the boiling temperature of the reaction mixture.

The compounds of the formula I obtained by the process according to the invention can be isolated from the reaction mixture by methods known per se. In many cases the compound of the formula I precipitates from the reaction mixture in the form of a salt or hydrate thereof and can be separated by filtration or centrifuging. If the product does not precipitate from the reaction mixture, it can be precipitated by adding another solvent, for example water or methanol, or by distilling off the organic solvent. The compounds of the formula I obtained, if desired, can be purified by recrystallization, chromatography, trans-precipitation or boiling with a suitable solvent.

Compounds of the formula I in which R and/or $R^1$ is other than hydrogen contain a centre of asymmetry and may be present in the form of optically active antipodes or racemates. The optically active antipodes of the compouds of the formula I can be prepared by starting from optically active compounds of the formula II.

Compounds of the formula II used as starting materials, wherein R, $R^1$, $R^2$, $R^3$ and X are as hereinbefore defined, are prepared by halogenation from compounds of the formula

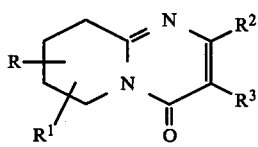

IV wherein R, $R^1$, $R^2$ and $R^3$ are as defined above [Arzneimittelforschung 22, 815 (1972)]. As a halognating agent elementary halogen, for example bromine, acid halides for example sulfuryl chloride, organic halogen derivatives, such as N-bromo-succinimide can be used. The reaction is conducted in an organic solvent, such as acetic acid, preferably at room temperature, optionally in the presence of an acid binding agent, for example sodium acetate.

The compounds of the formula I, in which
(a) $R^3$ is aralkyl or halogen and R, $R^1$, $R^2$, $R^4$ and $R^5$ are as hereinbefore defined, or
(b) $R^4$ is the group —$(CH_2)_m$—Het (m is the integer 1, 2 or 3, Het represents an optionally substituted heterocyclic group) and R, $R^1$, $R^2$, $R^3$ and $R^5$ are as hereinbefore defined,
are new compounds and together with their pharmaceutically acceptable salts, hydrates, stereoisomers, optically active isomers, geometric isomers, and tautomers are also within the scope of the present invention.

The antiallergic and antiasthmatic activity of the compounds of the formula I is particularly interesting.

The allergic reactions induced by the antigen-antibody interaction may occur in the different tissues and organs accompanied by different symptoms. The most frequent form of the allergy is asthma; as an antiasthmatic agent disodium chromoglycate [1,3-bis(2-carboxy-chromon-6-yl-ox)-2-hydroxypropane, Intal ®] is widely used, but is not active orally and it produces the desired effect only by using an inhaler, which makes administration rather complicated. We have now found that the compounds of the formula I cure the allergic symptoms both orally and intravenously as well as by inhaling.

The efficiency of the compounds of the formula I was proved by standard tests to determine antiallergic activity. The test is carried out by the PCA test-method (Ovary: J. Immun. 81, 355 (1958)) and the Church-test (British J. Pharm. 46, 56–66 (1972); Immunology 29, 527–534 (1975)) and for comparison disodium chromoglycate is used. The results obtained in PCA test are summarized in Table I.

TABLE I

| Compound | PCA test $ED_{50}$ $\mu$moles/$Kg^{i.v.}$ |
|---|---|
| 9-Phenylamino-6-methyl-4-oxo-6,7-dihydro-4H—pyrido[1,2-a]-pyrimidine-3-carboxylic acid | 1.3 |
| 6-Methyl-9-(2-methylphenyl-amino)-4-oxo-6,7-dihydro-4H—pyrido[1,2-a]pyrimidine-3-carboxylic acid | 5.4 |
| disodium chromoglycolate | 1.0 |

The above results show that the representatives of the compounds prepared according to the invention exhibit also oral activity, whereas disodium chromoglycolate is effective only when administered intravenously. Compounds of the formula I are more potent also when administered intravenously.

The toxicity of the compounds of the formula I is low, generally $LD_{50}$ 500 mg./kg. p.o. on rats and mice.

The compounds of the formula I may be employed in the form of pharmaceutical compositions containing the active ingredient in admixture with solid or liquid organic or inorganic carriers. The compositions are prepared by methods known per se.

The compositions may be formulated in a form suitable for oral, parenteral administration or for inspiration, such as tablets, dragées, capsules, lozenges, powders mixture, aerosol spray, aqueous suspension or solution, injection solution or syrup. The compositions may contain suitable solid diluents or carriers, sterilized aqueous solvents or non-toxic organic solvents. To the compositions for oral administration conventional flavoring or sweetening agents can be added.

As carriers for the tablets suitable for oral administration preferably lactose, sodium citrate, calcium carbonate and disintegrating substrates, such as starch, sodium lauryl sulfate, magnesium stearate are used. The carrier of the capsules preferably is lactose of polyethylene glycol. The aqueous suspensions may contain emulsifying and suspending agents. For dilution of the organic solvent suspensions ethanol, glycerin, chloroform, etc. can be used.

The compositions suitable for parenteral administration and inspiration are solutions or suspensions of the active ingredient in a suitable medium, e.g. peanut or sesame oil, polypropylene glycol or water. The injection compositions may be administered intramuscularly, intravenously or subscutaneously. The injection solutions are preferably prepared in an aqueous medium and the pH is adjusted to an appropriate value. The solutions may be prepared if desired, in the form of physiological saline or glucose solutions.

The compositions may be administered also by inhalation when curing asthma, by using the conventional inhalating and nebulizing equipment.

The active ingredient content of the pharmaceutical compositions may vary within a wide range and may be 0.005 to 90%.

The daily effective dose depends on the condition, age and weight of the patient and on type of formulation and activity of the active ingredient. The daily oral dosage level generally lies between 0.05 and 15 mg./kg. while the daily dosage level generally is 0.001 to 5 mg./kg. at once or in several portions a day when administered intravenously or by inspiration.

The above data are for orientation only, the exact doses should always be prescribed by the physician. Alterations in both directions are allowed.

Further details of the invention are illustrated by the following Examples which are given for illustration and not for limitation.

EXAMPLE 1

1.83 g. (0.005 moles) of 9,9-dibromo-6-methyl-4-oxo-6,7,8,9-tetrahydro-4H-pyrido[1,2-a]pyrimidine-3-carboxylic acid are dissolved in 5 ml. of dimethyl sulfoxide. To the solution 0.5 ml. (0.0055 moles) of aniline and 1.3 ml. (0.01 moles) of N,N-dimethylaniline are added. The reaction mixture is allowed to stand for three days, whereupon it is poured onto 20 ml. of water. The crystals are filtered off, washed with a small amount of water, dried and recrystallized from acetonitrile. 0.83 g. (55.8%) of 9-anilino-6-methyl-4-oxo-6,7-dihydro-4H-pyrido[1,2-a]pyrimidine-3-carboxylic acid are obtained, melting at 169° to 170° C.

Analysis for $C_{16}H_{15}N_3O_3$: calculated: C 64.64%, H 5.09%, N 14.13%; found: C 64.22%, H 5,08%, N 14.14%.

EXAMPLE 2

Following the procedure described in Example 1 but using pyridine instead of N,N-dimethylaniline as an acid binding agent, 9-anilino-6-methyl-4-oxo-6,7-dihydro-4H-pyrido[1,2-a]pyrimidine-3-carboxylic acid is obtained, melting at 170° to 171° C. Yield 47.1%. The product does not give any melting point depression when admixed with the product of Example 1.

EXAMPLE 3

1.83 g. (0.005 moles) of 9,9-dibromo-6-methyl-4-oxo-6,7,8,9-tetrahydro-4H-pyrido[1,2-a]pyrimidine-3-carboxylic acid are dissolved in 10 ml. of chloroform. To the solution 1.5 ml. (0.015 moles) of n-butylamine are added. The reaction mixture is allowed to stand for three days, whereupon 5 ml. of water are added. The pH of the aqueous phase is adjusted to 2 by a 5% by weight aqueous hydrochloric acid solution, under stirring. The organic phase is separated, the aqueous phase is extracted with two 5-ml. portions of chloroform. The combined organic phases are dried on anhydrous sodium sulfate, whereupon the solvent is distilled off in vacuo. The residue is recrystallized from methanol.

0.5 g. (36.1%) of 9-(n-butylamino)-6-methyl-4-oxo-6,7-dihydro-4H-pyrido[1,2-a]pyrimidine-3-carboxylic acid are obtained, melting at 135° to 137° C.

Analysis for $C_{14}H_{19}N_3O_3$: calculated: C 60.63%, H 6.91%, N 15.15%; found: C 60.92%, H 7.00%, N 15.20%.

EXAMPLE 4

Into 15 ml. of methanol 1.83 g. (0.005 moles) of 9,9-dibromo-6-methyl-4-oxo-6,7,8,9-tetrahydro-4H-pyrido[1,2-a]pyrimidine-3-carboxylic acid 1.4 ml. (0.015 moles) of aniline are weighed. The mixture is heated under stirring until a solution is obtained. The solution is cooled to room temperature and stirred for three days. The precipitated crystals are filtered off and washed with methanol.

0.8 g. (53.8%) of 9-anilino-6-methyl-4-oxo-6,7-dihydro-4H-pyrido[1,2-a]pyrimidine-3-carboxylic acid are obtained, melting at 172° to 173° C. The product does not give any melting point depression when admixed with the product of Example 1 or Example 2.

EXAMPLE 5

3.9 g. (0.01 moles) of 9,9-dibromo-6-methyl-4-oxo-6,7,8,9-tetrahydro-4H-pyrido[1,2-a]pyrimidine-3-carboxylic acid ethyl ester are dissolved in 30 ml. of dry ethanol. To the solution 3.3 ml. (0.03 moles) of N-methylaniline are added, whereupon the reaction mixture is refluxed for 8 hours.

When the reaction terminates, the solvent is distilled off under reduced pressure. To the residue 40 ml. of a 5% by weight hydrochloric acid solution are added, and the product is extracted with two 15-ml. portions of choroform. The combined organic phases are dried over anhydrous sodium hydroxide and evaporated in vacuo. The residue is recrystallized from methanol.

2.6 g. (76.6%) of 6-methyl-9-(N-methylamino)-4-oxo-6,7-dihydro-4H-pyrido[1,2-a]pyrimidine-3-carboxylic acid ethyl ester are obtained, melting at 141° to 142° C.

Analysis for $C_{19}H_{21}N_3O_3$: calculated: C 67.24%, H 6.23%, N 12.38%; found: C 67.50%, H 6.36%, N 12.41%.

EXAMPLE 6

Following the procedure described in Example 5 but replacing 9,9-dibromo-6-methyl-4-oxo-6,7,8,9-tetrahydro-4H-pyrido[1,2-a]pyrimidine-3-carboxylic acid ethyl ester by 9,9-dibromo-6-methyl-4-oxo-6,7,8,9-tetrahydro-4H-pyrido[1,2-a]pyrimidine-3-carboxylic acid, 6-methyl-9-(N-methylanilino)-4-oxo-6,7-dihydro-4H-pyrido[1,2-a]pyrimidine-3-carboxylic acid is obtained, melting at 170° to 171° C. Yield: 70.0%.

Analysis for $C_{17}H_{17}N_3O_3$: calculated: C 65.58%, H 5.50%, N 13.49%; found: C 65.22%, H 5.62%, N 13.37%.

EXAMPLE 7

19.7 g. (0.05 moles) of 9,9-dibromo-6-methyl-4-oxo-6,7,8,9-tetrahydro-4H-pyrido[1,2-a]pyrimidine-3-carboxylic acid ethyl ester are dissolved in 40 ml. of dimethyl sulfoxide, whereupon 13.7 ml. (0.15 moles) of aniline are added. The solution is allowed to stand for three days.

After standing it is diluted with 100 ml. of water and shaken with three 30-ml. portions of benzene. The combined organic phases are dried over anhydrous sodium sulfate and evaporated in vacuo. Recrystallization of the residue from ethanol yields 9.5 g. (58.4%) of 9-anilino-6-methyl-4-oxo-6,7-dihydro-4H-pyrido[1,2-a]pyrimidine-3-carboxylic acid ethyl ester, melting at 119° to 120° C.

Analysis for $C_{18}H_{19}N_3O_3$: calculated: C 66.45%, H 5.89%, N 12.91%; found: C 66.28%, H 5.81%, N 12.82%.

EXAMPLES 8 to 19

3.7 g. (0.01 moles) of 9,9-dibromo-6-methyl-4-oxo-6,7,8,9-tetrahydro-4H-pyrido[1,2-a]pyrimidine-3-carboxylic acid are dissolved in 5 ml. of dimethyl sulfoxide. To the solution 0.03 moles of an aromatic amine (see Table III) are added. The reaction mixture is allowed to stand for room temperature for three days. The precipitated crystals are filtered off. (If no crystallization can be observed, the product is precipitated from the reaction mixture by adding 20 ml. of water or 20 ml. of methanol.) The product is recrystallized from the solvent indicated in Table II.

TABLE II

| Example No. | Starting aniline | Product | Yield (%) | M.p. (°C.) | Solvent used for recrystallization | Formula | Analysis (%) Calculated C / H / N | Found C / H / N |
|---|---|---|---|---|---|---|---|---|
| 8 | aniline | 9-anilino-6-methyl-4-oxo-6,7-dihydro-4H—pyrido[1,2-a]pyrimidine-3-carboxylic acid | 60.0 | 172–3 | acetonitrile | $C_{16}H_{15}N_3O_3$ | 64.64 / 5.09 / 14.13 | 64.53 / 5.00 / 14.01 |
| 9 | o-toluidine | 6-methyl-9-(2-methylphenylamino)-4-oxo-6,7-dihydro-4H—pyrido[1,2-a]pyrimidine-3-carboxylic acid | 45.2 | 157–9 | methanol | $C_{17}H_{17}N_3O_3$ | 65.58 / 5.50 / 13.50 | 65.32 / 5.61 / 13.44 |
| 10 | p-phenetydine | 9-(4-ethoxyphenylamino)-6-methyl-4-oxo-6,7-dihydro-4H—pyrido[1,2-a]pyrimidine-3-carboxylic acid | 60.0 | 210–11 | acetonitrile | $C_{18}H_{19}N_3O_4$ | 63.33 / 5.61 / 12.31 | 63.22 / 5.55 / 12.21 |
| 11 | p-bromoaniline | 9-(4-bromo-phenylamino)-6-methyl-4-oxo-6,7-dihydro-4H—pyrido[1,2-a]pyrimidine-3-carboxylic acid | 68.2 | 202–204 | methanol | $C_{16}H_{14}N'O_3Br$ | 50.81 / 4.26 / 11.11 | 51.04 / 4.05 / 10.98 |
| 12 | m-chloroaniline | 9-(3-chloro-phenylamino)-6-methyl-4-oxo-6,7-dihydro-4H—pyrimido[1,2-a]pyrimidine-3-carboxylic acid | 33.7 | 170–2 | acetonitrile | $C_{16}H_{14}N_3O_3Cl$ | 57.92 / 4.25 / 12.67 | 57.76 / 4.15 / 12.59 |
| 13 | p-chloroaniline | 9-(4-chloro-phenylamino)-6-methyl-4-oxo-6,7-dihydro-4H—pyrido[1,2-a]pyrimidine-3-carboxylic acid | 82.5 | 202–3 | acetonitrile | $C_{16}H_{14}N_3O_3Cl$ | 57.92 / 4.25 / 12.67 | 57.82 / 4.30 / 12.79 |
| 14 | m-iodoaniline | 9-(3-iodo-phenylamino)-6-methyl-4-oxo-6,7-dihydro-4H—pyrido[1,2-a]pyrimidine-3-carboxylic acid | 24.2 | 229–30 | nitromethane | $C_{16}H_{14}N_3O_3I$ | 45.41 / 3.33 / 9.93 | 45.21 / 3.12 / 9.81 |
| 15 | m-nitroaniline | 6-methyl-9-(3-nitrophenylamino)-4-oxo-6,7-dihydro-4H—pyrido[1,2-a]pyrimidine-3-carboxylic acid | 23.1 | 204–6 | dimethylformamide | $C_{16}H_{14}N_4O_5$ | 56.14 / 4.12 / 16.36 | 55.95 / 4.09 / 16.30 |
| 16 | p-nitroaniline | 6-methyl-9-(4-nitrophenylamino)-4-oxo-6,7-dihydro-4H—pyrido-8 1,2-a]pyrimidine-3-carboxylic acid | 25.9 | 246–7 | dimethylformamide | $C_{16}H_{14}N_4O_5$ | 56.14 / 4.12 / 16.36 | 56.03 / 4.11 / 16.32 |
| 17[x] | aniline | (+)-9-anilino-6-methyl-4-oxo-6,7-dihydro-4H—pyrido[1,2-a]pyrimidine-3-carboxylic acid $[\alpha]_D^{20} = +90°$ (c = 1, chloroform) | 58.2 | 163–4 | acetonitrile | $C_{16}H_{15}N_3O_3$ | 64.64 / 5.09 / 14.13 | 64.41 / 4.97 / 13.99 |
| 18[xx] | aniline | (−)-9-anilino-6-methyl-4-oxo-6,7-dihydro-4H—pyrido[1,2-a]pyrimidine-3-carboxylic acid $[\alpha]_D^{20} = -90°$ (c = 1, chloroform) | 59.5 | 173–5 | acetonitrile | $C_{16}H_{15}N_3O_3$ | 64.64 / 5.09 / 14.13 | 64.71 / 5.12 / 14.20 |
| 19[xx] | p-bromoaniline | (−)-9-(4-bromo-phenylamino)-6-methyl-4-oxo-6,7-dihydro-4H—pyrido[1,2-a]pyrimidine-3-carboxylic $[\alpha]_D^{20} = -85°$ (c = 1, chloroform) | 62.2 | 214–5 | methanol | $C_{16}H_{14}N_3O_3Br$ | 50.81 / 4.26 / 11.11 | 50.62 / 4.13 / 11.09 |

[x] The product is prepared starting from optically active (+)-9,9-dibromo-6-methyl-4-oxo-6,7,8,9-tetrahydro-4H—pyrido[1,2-a]pyrimidine-3-carboxylic acid instead of racemic (±)-9,9-dibromo-6-methyl-4-oxo-6,7,8,9-tetrahydro-4H—pyrido[1,2-a]pyrimidine-3-carboxylic acid

[xx] The product is prepared starting from (−)-9,9-dibromo-6-methyl-4-oxo-6,7,8,9-tetrahydro-4H—pyrido[1,2-a]pyrimidine-3-carboxylic acid instead of racemic (±)-9,9-dibromo-6-methyl-4-oxo-6,7,8,9-tetrahydro-4H—pyrido[1,2-a]pyrimidine-3-carboxylic acid

EXAMPLE 20

Following the procedure described in Example 8 but replacing 9,9-dibromo-6-methyl-4-oxo-6,7,8,9-tetrahydro-4H-pyrido[1,2-a]pyrimidine-3-carboxylic acid by 9,9-dibromo-4-oxo-6,7,8,9-tetrahydro-4H-pyrido[1,2-a]pyrimidine-3-carboxylic acid, 9-(phenylamino)-4-oxo-6,7-dihydro-4H-pyrido[1,2-a]pyrimidine-3-carboxylic acid is obtained, melting at 197° to 198° C. after recrystallization from acetonitrile. Yield: 60.5%.

Anaylsis for $C_{15}H_{13}N_3O_3$: calculated: C 63.60%, H 4.63%, N 14.83%; found: C 63.42%, H 4.59%, N 14.70%.

EXAMPLES 21 TO 30

The procedure described in connection with Examples 8 to 19 is followed. The results are set forth in Table III.

TABLE III

| Example No. | Starting aniline | Product | Yield (%) | M.P. (°C.) | Solvent used for recrystal- lization | Formula | Analysis (%) Calculated C | H | Found N |
|---|---|---|---|---|---|---|---|---|---|
| 21 | 2-amino- phenol | 9-(2-hydroxyphenyl- amino)-6-methyl-4-oxo- 6,7-dihydro-4H—pyrido- [1,2-a]pyrimidine-3- carboxylic acid | 79.8 | 208–209 | ethanol | $C_{16}H_{15}N_3O_4$ | 61.34 4.83 61.29 4.90 | | 13.41 13.39 |
| 22 | 4- anyridine | 6-methyl-9-(4-methoxy- phenylamino)-4-oxo-6,7- dihydro-4H—pyrido- [1,2-a]pyrimidine-3- carboxylic acid | 81.1 | 195–196 | aceto- nitrile | $C_{17}H_{17}N_3O_4$ | 62.38 5.23 62.41 5.22 | | 12.84 12.90 |
| 23 | 4-amino- benzoic acid | 9-(4-carboxyphenyl- amino)-6-methyl-4-oxo- 6,7-dihydro-4H—pyrido- [1,2-a]pyrimidine-3- carboxylic acid | 78.3 | 230–231 | ethanol$^x$ | $C_{17}H_{15}N_3O_5$ | 59.80 4.40 59.19 4.25 | | 12.31 12.12 |
| 24 | 4-bi- phenyl- amine | 8-(4-biphenylamino)-6- methyl-4-oxo-6,7-di- hydro-4H—pyrido[1,2-a]- pyrimidine-3-carboxylic acid | 80.0 | 218–219 | ethanol$^x$ | $C_{22}H_{19}N_3O_3$ | 70.76 5.13 70.82 5.20 | | 11.25 11.22 |
| 25 | 3,4-di- chloro- aniline | 9-(3,4-dichlorophenyl- amino)-6-methyl-4-oxo- 6,7-dihydro-4H—pyrido- [1,2-a]pyrimidine-3- cabroxylic acid | 62.1 | 218–219 | ethanol$^x$ | $C_{16}H_{13}N_3O_3Cl_2$ | 52.48 3.58 52.31 3.49 | | 11.47 11.27 |
| 26 | 2-tetra- zolamine | 6-methyl-9-(2-tetra- zolylamino)-4-oxo- 6,7-dihydro-4H—pyrido- [1,2-a]pyrimidine-3- carboxylic acid | 23.1 | 215–217 | ethanol | $C_{11}H_{11}N_7O_3$ | 45.68 3.83 35.28 3.88 | | 33.90 34.10 |
| 27 | 3-amino- pyridine | 6-methyl-9-(3-pyridyl- amino)-4-oxo-6,7-di- hydro-4H—pyrido- [1,2-a]pyrimidine-3- carboxylic acid | 16.9 | 250 | ethanol$^x$ | $C_{15}H_{14}N_4O_3$ | 60.40 4.73 60.00 4.59 | | 18.79 18.61 |
| 28 | 3-bromo- aniline | 9-(3-bromophenyl- amino)-6-methyl-4-oxo- 6,7-dihydro-4H—pyrido- [1,2-a]pyrimidine-3- carboxylic acid | 69.9 | 174–175 | aceto- nitrile | $C_{16}H_{14}N_3O_3Br$ | 51.08 3.75 51.39 3.75 | | 11.17 11.11 |
| 29 | 3-iodo- aniline | 9-(3-iodophenyl-amino)- 6-methyl-4-oxo-6,7-di- hydro-4H—pyrido[1,2-a]- pyrimidine-3-carboxylic acid | 32.7 | 229–230 | nitro- methane | $C_{16}H_{14}N_3O_3I$ | 45.41 3.33 45.17 3.21 | | 9.93 9.82 |
| 30 | 1-naphthyl- amine | 6-methyl-9-(1-naphthyl- amino)-4-oxo-6,7-di- hydro-4H—pyrido- [1,2-a]pyrimidine-3- carboxylic acid | 65.6 | 221–222 | ethanol$^x$ | $C_{20}H_{17}N_3O_3$ | 69.15 4.93 69.29 5.02 | | 12.09 12.15 |

We claim:

1. A process for the preparation of a compound of the formula (I)

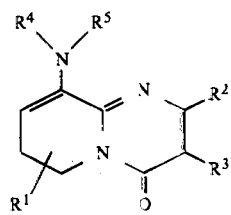

wherein $R^1$ and $R^2$ are each hydrogen or lower alkyl;

$R^3$ is carboxy, lower alkoxycarbonyl, carbamoyl, carbamoyl substituted by one or two lower alkyl groups, or cyano;

$R^4$ is hydrogen, lower alkyl, phenyl, naphthyl, phenyl or naphthyl substituted by at least one fluoro, chloro, bromo, iodo, lower alkyl, lower alkoxy, hydroxy, carboxy, or phenyl, pyridyl or tetrazolyl; and $R^5$ is hydrogen or lower alkyl; or a pharmaceutically acceptable salt, hydrate, stereoisomer, optically active isomer, geometric isomer, or tautomer thereof, which comprises the step of aminating a racemic or optically active compound of the formula (II)

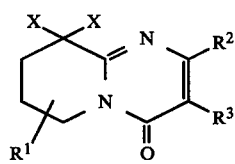

wherein

X is halogen with a compound of the formula (III)

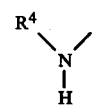

or a pharmaceutically acceptable acid addition salt thereof.

2. The process defined in claim 1 wherein a compound of the formula II in which X is chlorine or bromine, is used as a starting material.

3. The process defined in claim 1 wherein 1 to 3 molar equivalents of a compound of the formula III or an acid-addition salt thereof are used relative to the compound of the formula II.

4. The process defined in claim 1 wherein the reaction is carried out in an inert organic solvent.

5. The process defined in claim 4 wherein the reaction is carried out in an alkanol or halogenated hydrocarbon or organic acid nitrile.

6. The process defined in claim 4 wherein the reaction is carried out in dimethyl sulfoxide.

7. The process defined in claim 1 wherein the reaction is effected in the presence of an acid binding agent.

8. The process defined in claim 7 wherein a tertiary amine or pyridine is used as acid binding agent.

* * * * *